(12) United States Patent
Qian et al.

(10) Patent No.: US 12,187,710 B2
(45) Date of Patent: Jan. 7, 2025

(54) SALT OF SYK INHIBITOR AND CRYSTALLINE FORM THEREOF

(71) Applicant: CHIA TAI TIANQING PHARMACEUTICAL GROUP CO., LTD., Lianyungang (CN)

(72) Inventors: Wenyuan Qian, Nanjing (CN); Hongjian Wang, Nanjing (CN); Ming Zhang, Nanjing (CN); Fei Liu, Lianyungang (CN); Lei Xing, Lianyungang (CN); Zhongyuan Hu, Lianyungang (CN); Yahui Guo, Lianyungang (CN); Yanlong Liu, Lianyungang (CN); Huihui Zhang, Lianyungang (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 881 days.

(21) Appl. No.: 17/309,646

(22) PCT Filed: Dec. 13, 2019

(86) PCT No.: PCT/CN2019/125157
§ 371 (c)(1),
(2) Date: Jun. 11, 2021

(87) PCT Pub. No.: WO2020/119785
PCT Pub. Date: Jun. 18, 2020

(65) Prior Publication Data
US 2022/0017498 A1    Jan. 20, 2022

(30) Foreign Application Priority Data
Dec. 14, 2018    (CN) .......................... 201811533849.X

(51) Int. Cl.
C07D 405/14    (2006.01)

(52) U.S. Cl.
CPC ........ *C07D 405/14* (2013.01); *C07B 2200/13* (2013.01)

(58) Field of Classification Search
CPC .......................... C07D 405/14; C07B 2200/13
See application file for complete search history.

(56) References Cited

U.S. PATENT DOCUMENTS

| 11,091,460 B2 * | 8/2021 | Liu .......................... A61P 29/00 |
| 2008/0119515 A1 | 5/2008 | Siddiqui |

(Continued)

FOREIGN PATENT DOCUMENTS

| AU | 2018286247 A1 | 1/2020 | |
| CN | 1784229 A * | 6/2006 | ................ A61P 1/00 |

(Continued)

OTHER PUBLICATIONS

Gupta D, Bhatia D, Dave V, Sutariya V, Varghese Gupta S. Salts of Therapeutic Agents: Chemical, Physicochemical, and Biological Considerations. Molecules. Jul. 14, 2018;23(7) (Year: 2018).*

(Continued)

*Primary Examiner* — Clinton A Brooks
*Assistant Examiner* — Izabela Schmidt
(74) *Attorney, Agent, or Firm* — NIXON PEABODY LLP

(57) ABSTRACT

Provided is a salt of an Syk inhibitor and a crystalline form thereof, and more specifically, provided are 5-fluoro-1-methyl-3-((5-(4-(oxetan-3-yl)piperazine-1)-yl)pyridin-2-yl)amino)-6-(1H-pyrazol-3-yl)quinoline-2(1H)-ketamine hydrochloride, a crystalline form thereof, a preparation method therefor, a pharmaceutical composition thereof and a use thereof. The hydrochloride of the compound represented by formula I and the crystalline form thereof have good salt-forming properties, high stability and low hygro- (Continued)

scopicity, have advantages in terms of physical properties, safety and metabolic stability, and have value in prepared medicines.

17 Claims, 3 Drawing Sheets

(56) References Cited

U.S. PATENT DOCUMENTS

| | | | | |
|---|---|---|---|---|
| 2010/0204470 | A1* | 8/2010 | Wieser | C07D 307/87 |
| | | | | 564/336 |
| 2016/0176869 | A1 | 6/2016 | Chen | |
| 2018/0312496 | A1 | 11/2018 | Samajdar | |
| 2019/0359616 | A1 | 11/2019 | Kawahata | |
| 2020/0199101 | A1* | 6/2020 | Liu | C07D 413/14 |

FOREIGN PATENT DOCUMENTS

| | | |
|---|---|---|
| CN | 107810185 A | 3/2018 |
| WO | WO 2016/097862 | 6/2016 |
| WO | WO-2016168444 A1 * | 10/2016 ........... A61K 31/505 |
| WO | WO 2018/005849 A1 | 1/2018 |
| WO | 2018097234 A1 | 5/2018 |
| WO | WO 2018/228475 A1 | 12/2018 |

OTHER PUBLICATIONS

CN-1784229-A—Machine English Translation—downloaded from Google Patents Jun. 2024 (Year: 2024).*
Crawford et al. "Discovery of GDC-0853: a potent, selective, and noncovalent Bruton's tyrosine kinase inhibitor in early clinical development." Journal of Medicinal Chemistry. pp. 2227-2245. (2018).
O'Brien, N. J. et al., "Synthesis and biological evaluation of substituted 3-anilino-quinolin-2(1H)-ones as PDK1 inhibitors," Bioorganic & Medicinal Chemistry, 22(14): 3781-3790, Jul. 15, 2014.
International Search Report in International Application No. PCT/CN2019/125157, mailed Mar. 16, 2020 (4 pages).
Supplementary European Search Report—EPO—EP application 19897084, Dated Aug. 9, 2022.

* cited by examiner

SALT OF SYK INHIBITOR AND CRYSTALLINE FORM THEREOF

CROSS-REFERENCE TO RELATED APPLICATIONS

The present application is a U.S. national stage of PCT/CN2019/125157, filed on December 13, 2019, which claims priority and benefit to the Chinese Patent Application No. 201811533849.X filed with China National Intellectual Property Administration on Dec. 14, 2018, each of the disclosures is incorporated herein by reference in its entirety.

TECHNICAL FIELD

The present application belongs to the field of medical chemistry, relates to a salt of a Syk inhibitor and a crystalline form thereof, and more particularly relates to a 5-fluoro-1-methyl-3-((5-(4-(oxetan-3-yl)piperazin-1-yl)pyridin-2-yl)amino)-6-(1H-pyrazol-3-yl)quinolin-2(1H)-one hydrochloride and a crystalline form thereof, and a preparation method therefor, a pharmaceutical composition thereof and use thereof.

BACKGROUND

Spleen tyrosine kinase (Syk) is an intracellular tyrosine protein kinase and belongs to the ZAP70 protein kinase family. Syk plays a key role in early development of B cells, lymphocyte ontogenesis, and functioning of mature B cells. During this process, it is involved in a variety of signal transduction pathways and functions without phosphorylation by Src kinase. Syk, in addition to being ubiquitously expressed in hematopoietic stem cells, is expressed in non-hematopoietic cells such as epithelial cells, hepatocytes, fibroblasts, neural cells and breast tissue, and it has various functions.

Dysfunction of Syk PTK is found in many human diseases such as allergic reactions, asthma, inflammation and autoimmune diseases, and numerous studies have shown that Syk is an important mediator in acute or chronic inflammation. Activation of Syk is found in several common B cell malignant tumors. For example, antigen independent phosphorylated Syk is detectable in follicular lymphoma, diffuse large B-cell lymphoma, mantle cell lymphoma and B cell chronic lymphocytic leukemia. Researchers have found that inhibition of Syk in cells of follicular lymphoma and diffuse large B-cell lymphoma can reduce the level of phosphorylation of downstream signaling molecules, thereby inhibiting tumor cell proliferation and survival. In addition, Syk translocations have been found in myelodysplastic syndrome and peripheral T-cell lymphoma, further suggesting that the kinase can act as a proto-oncogene. Inhibition of Syk activity can therefore be used to treat specific types of cancers including B cell lymphoma and leukemia.

SUMMARY

Provided is a compound of formula I having the chemical name as follows: 5-fluoro-1-methyl-3-((5-(4-(oxetan-3-yl)piperazin-1-yl)pyridin-2-yl)amino)-6-(1H-pyrazol-3-yl)quinolin-2(1H)-one,

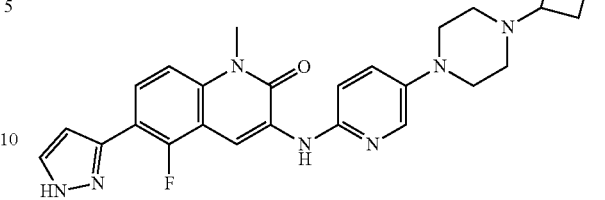

(I)

In one aspect, the present application provides a hydrochloride of a compound of formula I.

In some embodiments, the hydrochloride of the compound of formula I is a 1:1 hydrochloride of the compound of formula I (formula II),

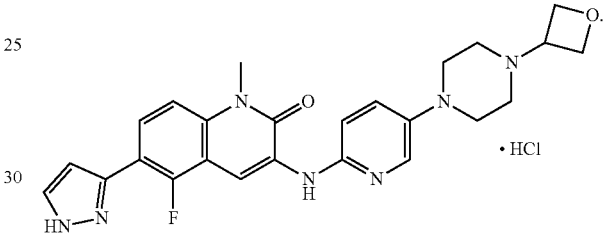

(II)

The hydrochloride of the compound of formula I described herein may be in crystalline form or amorphous form, preferably in crystalline form.

The crystalline form of the hydrochloride of the compound of formula I features high stability, small hygroscopicity, better in vivo metabolism level, longer half-life period, better inhibition activity on spleen tyrosine kinase, better properties in physical property, safety and metabolic stability and higher druggability.

In some embodiments, the hydrochloride of the compound of formula I disclosed herein is a form A crystal characterized by having diffraction peaks represented by 2θ values at about 4.9°, 10.1°, 12.2°, 15.5°, 19.6° and 23.8° in an X-ray powder diffraction spectrum; typically, having diffraction peaks represented by 2θ values at about 4.9°, 10.1°, 12.2°, 15.5°, 17.8°, 19.2°, 19.6°, 22.9°, 23.8° and 25.6° in an X-ray powder diffraction spectrum; typically, having diffraction peaks represented by 2θ values at about 4.9°, 9.6°, 10.1°, 12.2°, 15.5°, 16.3°, 17.8°, 19.2°, 19.6°, 20.4°, 22.9°, 23.3°, 23.8°, 25.6°, 26.8°, 27.4°, 29.0° and 36.8 in an X-ray powder diffraction spectrum; and typically, having diffraction peaks represented by 2θ values at about 4.9°, 9.6°, 10.1°, 12.2°, 14.4°, 15.5°, 16.3°, 17.3°, 17.8°, 19.2°, 19.6°, 20.4°, 22.9°, 23.3°, 23.8°, 25.6°, 26.8°, 27.4°, 28.3°, 29.0°, 31.2°, 31.6°, 31.9°, 32.3°, 33.0°, 34.3° and 36.8° in an X-ray powder diffraction spectrum.

As one embodiment of the present application, the peak positions and intensities of the characteristic peaks in an X-ray powder diffraction spectrum for form A crystal of the hydrochloride of the compound of formula I disclosed herein are shown in Table 1:

TABLE 1

XRPD pattern characterization data for form A crystal

| Number | Diffraction angle 2θ (°) | Relative strength (%) |
|---|---|---|
| 1 | 4.89 | 27.2 |
| 2 | 9.64 | 8.6 |
| 3 | 10.11 | 68.4 |
| 4 | 12.17 | 20.3 |
| 5 | 14.43 | 2.4 |
| 6 | 15.50 | 100 |
| 7 | 16.25 | 6.3 |
| 8 | 17.30 | 4.7 |
| 9 | 17.78 | 10.1 |
| 10 | 19.21 | 12.6 |
| 11 | 19.64 | 18.5 |
| 12 | 20.35 | 6.5 |
| 13 | 22.86 | 10.4 |
| 14 | 23.34 | 6 |
| 15 | 23.80 | 17.9 |
| 16 | 25.62 | 13.5 |
| 17 | 26.76 | 8.7 |
| 18 | 27.43 | 7.6 |
| 19 | 28.30 | 4.1 |
| 20 | 28.99 | 7.1 |
| 21 | 31.20 | 3.3 |
| 22 | 31.55 | 3 |
| 23 | 31.93 | 3.6 |
| 24 | 32.30 | 1.9 |
| 25 | 32.99 | 4.1 |
| 26 | 34.26 | 2.8 |
| 27 | 36.82 | 5.1 |

In one embodiment of the present application, provided is a form A crystal of the hydrochloride of the compound of formula I, which has an X-ray powder diffraction pattern as shown in FIG. 1.

In one embodiment of the present application, provided is a form A crystal of the hydrochloride of the compound of formula I, which has an absorption peak at about 272° C. in a differential scanning calorimetry (DSC) pattern.

In one embodiment of the present application, provided is a form A crystal of the hydrochloride of the compound of formula I, which has a DSC pattern as shown in FIG. 2.

In one embodiment of the present application, provided is a form A crystal of the hydrochloride of the compound of formula I, which has a thermogravimetric analysis (TGA) pattern as shown in FIG. 3.

In some embodiments, the hydrochloride of the compound of formula I disclosed herein is a form B crystal characterized by having diffraction peaks represented by 2θ values at about 5.2°, 10.4°, 14.7°, 15.5° and 25.3° in an X-ray powder diffraction spectrum; typically, having diffraction peaks represented by 2θ values at about 5.2°, 10.4°, 14.7°, 15.5°, 16.5°, 20.7°, 21.5°, 22.8°, 25.3° and 27.9° in an X-ray powder diffraction spectrum; typically, having diffraction peaks represented by 2θ values at about 5.2°, 10.4°, 14.7°, 15.5°, 16.5°, 17.1°, 17.5°, 20.3°, 20.7°, 21.5°, 22.8°, 23.8°, 24.7°, 25.3°, 27.5°, 27.9° and 31.2° in an X-ray powder diffraction spectrum; and typically, having diffraction peaks represented by 2θ values at about 5.2°, 10.4°, 13.1°, 14.7°, 15.5°, 16.5°, 17.1°, 17.5°, 20.0°, 20.3°, 20.7°, 21.5°, 22.8°, 23.2°, 23.8°, 24.7°, 25.3°, 25.9°, 26.2°, 27.5°, 27.9°, 28.2°, 29.7°, 30.0°, 30.3°, 31.2°, 31.7°, 32.3°, 34.5°, 34.9° and 36.6° in an X-ray powder diffraction spectrum.

As one embodiment of the present application, the peak positions and intensities of the characteristic peaks in an X-ray powder diffraction spectrum for form B crystal of the hydrochloride of the compound of formula I disclosed herein are shown in Table 2:

TABLE 2

XRPD pattern characterization data for form B crystal

| Number | Diffraction angle 2θ (°) | Relative strength (%) |
|---|---|---|
| 1 | 5.20 | 44.4 |
| 2 | 10.35 | 52.2 |
| 3 | 13.09 | 7.3 |
| 4 | 14.74 | 59.8 |
| 5 | 15.50 | 67.8 |
| 6 | 16.50 | 22 |
| 7 | 17.14 | 12.5 |
| 8 | 17.45 | 10.4 |
| 9 | 20.02 | 5.0 |
| 10 | 20.33 | 17.1 |
| 11 | 20.72 | 45.2 |
| 12 | 21.52 | 46.4 |
| 13 | 22.78 | 29.3 |
| 14 | 23.21 | 8.2 |
| 15 | 23.78 | 18.0 |
| 16 | 24.67 | 18.2 |
| 17 | 25.34 | 100 |
| 18 | 25.92 | 7.4 |
| 19 | 26.22 | 6.2 |
| 20 | 27.47 | 14.8 |
| 21 | 27.89 | 51.1 |
| 22 | 28.18 | 9.8 |
| 23 | 29.66 | 4.7 |
| 24 | 30.04 | 8.7 |
| 25 | 30.31 | 7.8 |
| 26 | 31.22 | 10.1 |
| 27 | 31.73 | 4.7 |
| 28 | 32.31 | 5.4 |
| 29 | 34.45 | 4.7 |
| 30 | 34.91 | 4.7 |
| 31 | 36.64 | 4.7 |

In one embodiment of the present application, provided is a form B crystal of the hydrochloride of the compound of formula I, which has an X-ray powder diffraction pattern as shown in FIG. 4.

In another aspect, the present application provides a method for preparing a form A crystal of the hydrochloride of the compound of formula I, comprising: (1) adding the compound of formula I into a preheated solvent, then adding another solvent dropwise until the solution is clear, and stirring while maintaining the temperature; (2) adding diluted hydrochloric acid dropwise into the solution of step (1), and stirring overnight while maintaining the temperature; and (3) slowly adding a solvent dropwise into the solution of step (2), stirring to precipitate a solid, filtering, and drying to give the form A crystal of the hydrochloride of the compound of formula I.

In one embodiment of the present application, in the above preparation of the form A crystal of the hydrochloride of the compound of formula I, the preheated solvent in step (1) is selected from the group consisting of water, ethyl acetate, dichloromethane, ethanol, acetone, acetonitrile, tetrahydrofuran and methyl tert-butyl ether; preferably, the preheated solvent is water or ethyl acetate.

In one embodiment of the present application, in the above preparation of the form A crystal of the hydrochloride of the compound of formula I, the preheated solvent in step (1) is at 30-40° C., preferably at 35-38° C.

In one embodiment of the present application, in the above preparation of the form A crystal of the hydrochloride of the compound of formula I, the another solvent in step (1) is selected from the group consisting of formic acid, acetic acid, propionic acid and oxalic acid; preferably, the another solvent is formic acid.

In one embodiment of the present application, in the above preparation of the form A crystal of the hydrochloride of the compound of formula I, the molar volume ratio of the compound of formula I to the another solvent in step (1) is 1 mmol:0.8 mL to 1 mmol:1.5 mL, preferably 1 mmol:0.8 mL to 1 mmol:1.2 mL, and more preferably 1 mmol:0.8 mL to 1 mmol:1.0 mL.

In one embodiment of the present application, in the above preparation of the form A crystal of the hydrochloride of the compound of formula I, the volume ratio of the preheated solvent to the another solvent in step (1) is 0.5:1 to 3:1, preferably 0.5:1 to 2:1.

In one embodiment of the present application, in the above preparation of the form A crystal of the hydrochloride of the compound of formula I, the molar ratio of hydrochloric acid in the diluted hydrochloric acid in step (2) to the compound of formula I in step (1) is 1:1 to 3:1, preferably 1:1 to 2:1.

In one embodiment of the present application, in the above preparation of the form A crystal of the hydrochloride of the compound of formula I, the concentration of the diluted hydrochloric acid in step (2) is 1-2 mol/L, preferably 1-1.2 mol/L; the diluted hydrochloric acid is obtained by diluting commercially available concentrated hydrochloric acid with water, or the diluted hydrochloric acid refers to a mixed solution of commercially available concentrated hydrochloric acid and another solvent same as the preheated solvent in step (1).

In one embodiment of the present application, in the above preparation of the form A crystal of the hydrochloride of the compound of formula I, the solvent in step (3) is selected from the group consisting of methanol, ethanol, acetone, isopropanol, acetonitrile, tetrahydrofuran, ethylene glycol or propylene glycol; preferably, the solvent is ethanol.

In one embodiment of the present application, in the above preparation of the form A crystal of the hydrochloride of the compound of formula I, the molar volume ratio of the solvent in step (3) to the compound of formula I in step (1) is 2 mL:1 mmol to 10 mL:1 mmol, preferably 4 mL:1 mmol to 9 mL:1 mmol.

In the above preparation of the form A crystal of the hydrochloride of the compound of formula I, the "maintaining the temperature" in step (1) and step (2) means that the stirring temperature is maintained at the same temperature as the preheated solvent in step (1).

In another aspect, the present application further provides a method for preparing a form B crystal of the hydrochloride of the compound of formula I, comprising: (1) adding the compound of formula I into a solvent and stirring for dissolving; (2) adding diluted hydrochloric acid into the solution of step (1) and stirring overnight; and (3) centrifuging the solution of step (2), and drying the solid to give the form B crystal of the hydrochloride of the compound of formula I.

In one embodiment of the present application, in the above preparation of the form B crystal of the hydrochloride of the compound of formula I, the solvent in step (1) is selected from the group consisting of methanol, ethanol, isopropanol, acetic acid, acetone, acetonitrile or a mixed solvent of any two thereof, preferably, the solvent is ethanol, acetic acid, acetone or a mixed solvent of any two thereof, and more preferably, the solvent ethanol is ethanol, a mixed solvent of ethanol and acetic acid, or a mixed solvent of acetone and acetic acid.

In one embodiment of the present application, in the above preparation of the form B crystal of the hydrochloride of the compound of formula I, the molar volume ratio of the compound of formula I to the another solvent in step (1) is 1 mmol:10 mL to 1 mmol:40 mL, preferably 1 mmol:20 mL to 1 mmol:35 mL.

In one embodiment of the present application, in the above preparation of the form B crystal of the hydrochloride of the compound of formula I, the solvent in step (1) is a mixed solvent of acetic acid and ethanol or a mixed solvent of acetic acid and acetone, wherein the volume ratio of acetic acid to ethanol or acetic acid to acetone is 1:5 to 1:10, preferably 1:5 to 1:8.

In one embodiment of the present application, in the above preparation of the form B crystal of the hydrochloride of the compound of formula I, the molar ratio of the compound of formula I in step (1) to the hydrochloric acid in step (2) is 1:1 to 1:5, preferably 1:1 to 1:3.5.

In one embodiment of the present application, in the above preparation of the form B crystal of the hydrochloride of the compound of formula I, the concentration of the diluted hydrochloric acid in step (2) is 1-2 mol/L, preferably 1-1.2 mol/L; the diluted hydrochloric acid is obtained by diluting commercially available concentrated hydrochloric acid with water.

In another aspect, the present application provides a hydrochloride of the compound of formula I, wherein the form A crystal of the hydrochloride of the compound of formula I accounts for 50% or more, preferably 75% or more, more preferably 90% or more and most preferably 95% or more of the weight of the hydrochloride of the compound of formula I. The hydrochloride of the compound of formula I may also comprise small amount of other crystalline or amorphous forms of the hydrochloride of the compound of formula I, for example, small amount of form B crystal of the hydrochloride of the compound of formula I.

In another aspect, the present application provides a hydrochloride of the compound of formula I, wherein the form B crystal of the hydrochloride of the compound of formula I accounts for 50% or more, preferably 75% or more, more preferably 90% or more and most preferably 95% or more of the weight of the hydrochloride of the compound of formula I.

In another aspect, the present application provides a pharmaceutical composition comprising a therapeutically effective amount of the hydrochloride of the compound of formula I described above; the pharmaceutical composition may comprise at least one pharmaceutically acceptable carrier or other excipient.

In another aspect, the present application provides use of the hydrochloride of the compound of formula I or the pharmaceutical composition described above in preparing a medicament for treating a disease related to Syk receptor.

In another aspect, the present application provides a method for treating a disease related to Syk receptor, comprising administering to a mammal in need a therapeutically effective amount of the hydrochloride of the compound of formula I or the pharmaceutical composition described above.

In another aspect, the present application provides the hydrochloride of the compound of formula I or the pharmaceutical composition described above for use in treating a disease related to Syk receptor in a mammal.

In some embodiments of the present application, the mammal is a human.

In the present application, the pharmaceutical composition can be formulated into a certain dosage form, and the administration route is preferably oral administration, parenteral administration (including subcutaneous, intramuscular and intravenous administration), rectal administration, and the like. For example, suitable dosage forms for oral administration include tablets, capsules, granules, pulvises, pills, powders, pastilles, syrups or suspensions; suitable dosage forms for parenteral administration include aqueous or non-aqueous solutions or emulsions for injection; suitable dosage forms for rectal administration include suppositories with hydrophilic or hydrophobic carriers. The dosage forms may also be formulated as desired for rapid, delayed or modified release of the active ingredient.

In some embodiments of the present application, the disease related to Syk receptor is selected from cancer and inflammatory diseases.

In some embodiments of the present application, the disease related to Syk receptor is selected from B-cell lymphoma, Hodgkin's lymphoma, non-Hodgkin's lymphoma, hairy cell leukemia, multiple myeloma, chronic granulocytic leukemia, acute granulocytic leukemia, chronic lymphocytic leukemia, acute lymphocytic leukemia, rheumatoid arthritis, allergic rhinitis, chronic obstructive pulmonary disease (COPD), adult respiratory distress syndrome (ARDs), allergy-induced inflammatory diseases, multiple sclerosis, autoimmune diseases, acute inflammatory reactions, allergic disorders and polycystic kidney disease.

In the present application, the X-ray powder diffraction spectrum of a sample is measured under the following conditions: instrument: Bruker D8 ADVANCE X-ray diffractometer; target: Cu:Kα; wavelength λ=1.54056 Å; range of 2θ angle: 4°-40°; scanning speed: 10°/min; rotation speed of sample: 15 rpm; Cu-target tube pressure and current: 40 KV, 40 mA.

In the present application, the DSC spectrum is measured under the following conditions: instrument: TA Q2000 differential scanning calorimeter; temperature range: 30-300° C.; heating rate: 10° C./min.

In the present application, the thermogravimetric analysis (TGA) is measured under the following conditions: instrument: TA Q5000 thermogravimetric analyzer; temperature range: 25-300° C.; heating rate: 10° C./min.

It should be noted that in X-ray powder diffraction spectrum, the diffraction pattern acquired from a crystal compound is generally characteristic for a particular crystal, where the relative intensities of the bands (especially at lower angles) may vary due to dominant orientation effects arising from differences in crystallization conditions, particle size and other measurement conditions. Therefore, the relative intensities of the diffraction peaks are not characteristic for the crystal concerned, and it is important to consider the relative positions of the peaks rather than their relative intensities for determining whether it is the same as a known crystal. In addition, there may be slight errors in the peak positions for any given crystal, as is also well known in the field of crystallography. For example, the position of the peak may shift due to temperature changes, sample movement or calibration of the instrument when analyzing a sample, and the error in the measurement of 2θ value is sometimes about ±0.2°. Therefore, this error should be considered when determining a crystalline structure. In XRD pattern, the peak position is usually represented by 2θ angle or crystal plane distance d, and there is a simple conversion relationship between the two: d=λ/2 sin θ, wherein d represents the crystal plane distance, λ represents the wavelength of the incident X-ray, and θ is the diffraction angle. For the same crystal of the same compound, the peak positions of the XRD patterns are similar in general, while the error in relative intensities may be large. It should also be noted that in the identification of mixtures, a portion of the diffraction lines may be absent due to, for example, reduce in the content, in which case it is not necessary to rely on all the bands observed in a high-purity sample, and even one band may be characteristic for a given crystal.

DSC measures the transition temperature when a crystalline form absorbs or releases heat due to a change in crystalline structure or melting of the crystalline form. For the same crystal of the same compound, the error of thermal transition temperature and melting point in successive analyses is typically within about 5° C., usually within about 3° C., or within about 2° C., and a given DSC peak or melting point of a compound, when referred to, means the DSC peak or melting point±5° C. DSC provides an auxiliary method to identify different crystal. Different crystalline morphologies can be identified by their different transition temperature characteristics. It should be noted that for a mixture, its DSC peak or melting point may vary over a larger range. Furthermore, melting temperature is related to heating rate.

Definitions and Description

As used in the specification and claims of the present application, the following terms, unless otherwise specified, have the meanings indicated:

"Mammal" includes human, domestic animals such as laboratory mammals and domestic pets (e.g., cat, dog, pig, cow, sheep, goat, horse, rabbit), and non-domesticated mammals such as wild mammals.

The term "pharmaceutical composition" refers to a formulation of the compound disclosed herein with a vehicle commonly recognized in the art for delivering a biologically active compound to a mammal, such as a human. The vehicle includes all pharmaceutically acceptable carriers for its use. The pharmaceutical composition facilitates administration of the compound to an organism.

The term "therapeutically effective amount" refers to an amount of a drug or a medicament that is sufficient to provide the desired effect but is non-toxic. The determination of the effective amount varies from person to person, depending on the age and general condition of a subject and also depending on the particular active substance. The appropriate effective amount in a case may be determined by those skilled in the art in the light of routine tests.

The term "pharmaceutically acceptable carriers" refers to those which are administered together with the active ingredient, do not have a significant irritating effect on an organism and do not impair the biological activity and properties of the active compound. For additional information on carriers, reference may be made to Remington: The Science and Practice of Pharmacy, 21st Ed., Lippincott, Williams & Wilkins (2005), the content of which is incorporated herein by reference.

As used herein, unless otherwise stated, the terms "comprise", "comprises" and "comprising" or equivalents thereof are open-ended statements and mean that elements, components and steps that are not specified may be included in addition to those listed.

All patents, patent applications and other identified publications are expressly incorporated herein by reference for the purpose of description and disclosure. These publications are provided solely because they were disclosed prior to the filing date of the present application. All statements as to the dates of these documents or description as to the contents of these documents are based on the information available to the applicant and do not constitute any admission as to the correctness of the dates of these documents or the contents of these documents. Moreover, in any country or region, any reference to these publications herein is not to be construed as an admission that the publications form part of the commonly recognized knowledge in the art.

DETAILED DESCRIPTION

Figure 1:
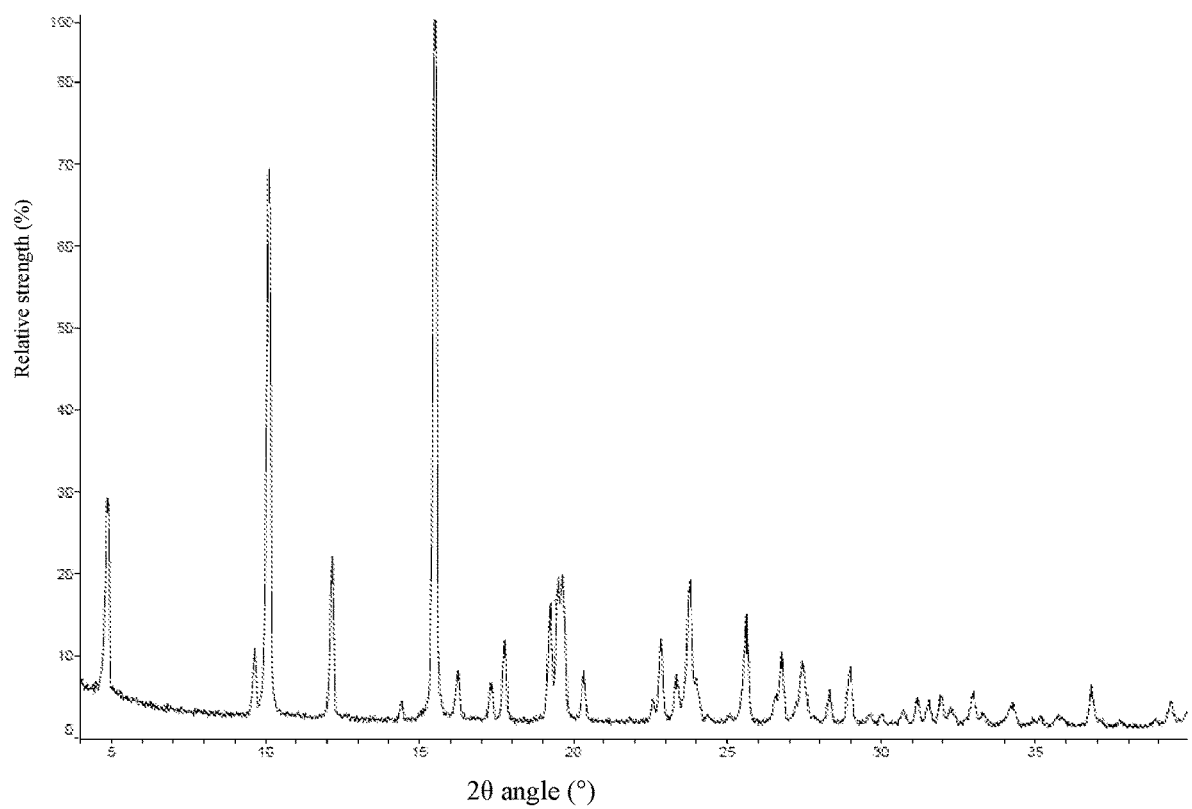
FIG. 1 is an X-ray powder diffraction (XRPD) pattern of the form A crystal of the hydrochloride of formula II in Example 2.
Figure 2:
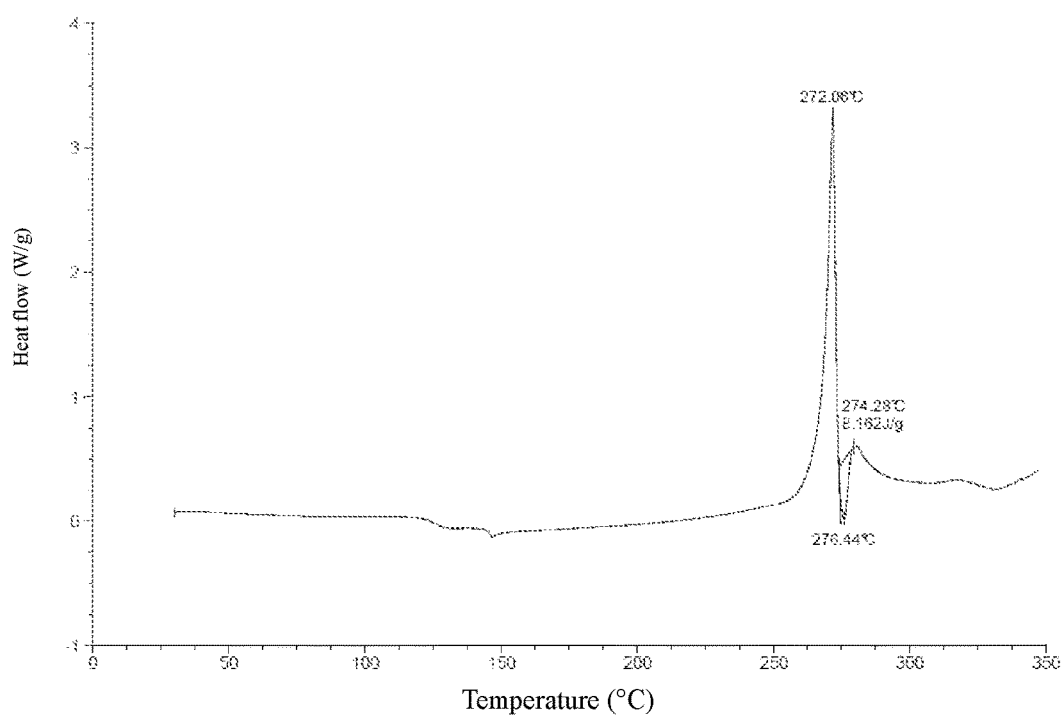
FIG. 2 is a differential scanning calorimetry (DSC) pattern of the form A crystal of the hydrochloride of formula II in Example 2.
Figure 3:
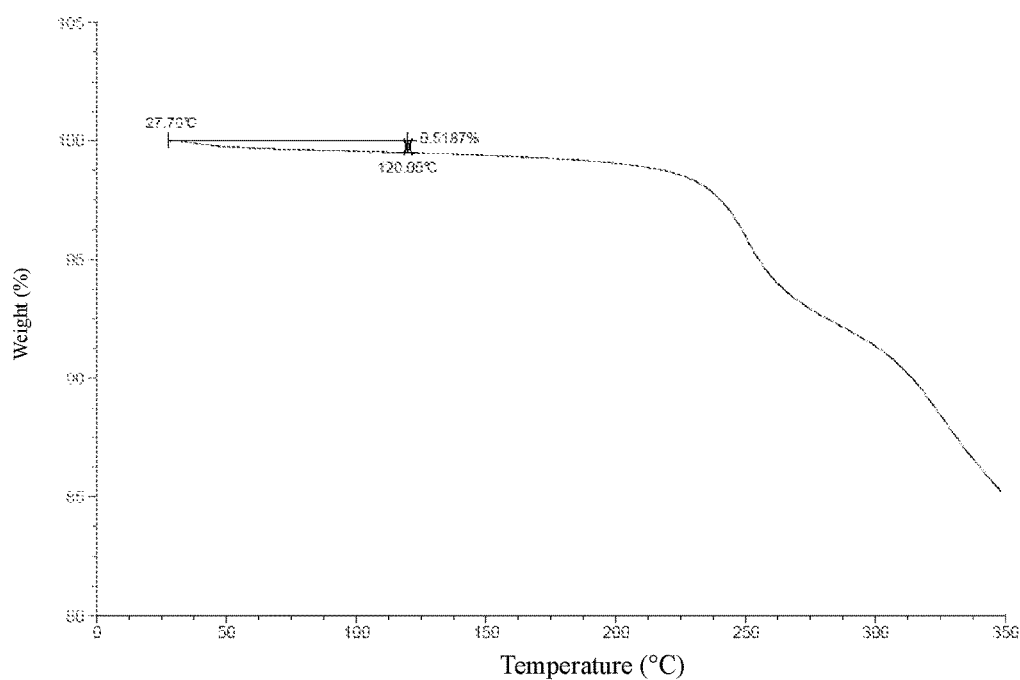
FIG. 3 is a thermogravimetric analysis (TGA) pattern of the form A crystal of the hydrochloride of formula II in Example 2.
Figure 4:
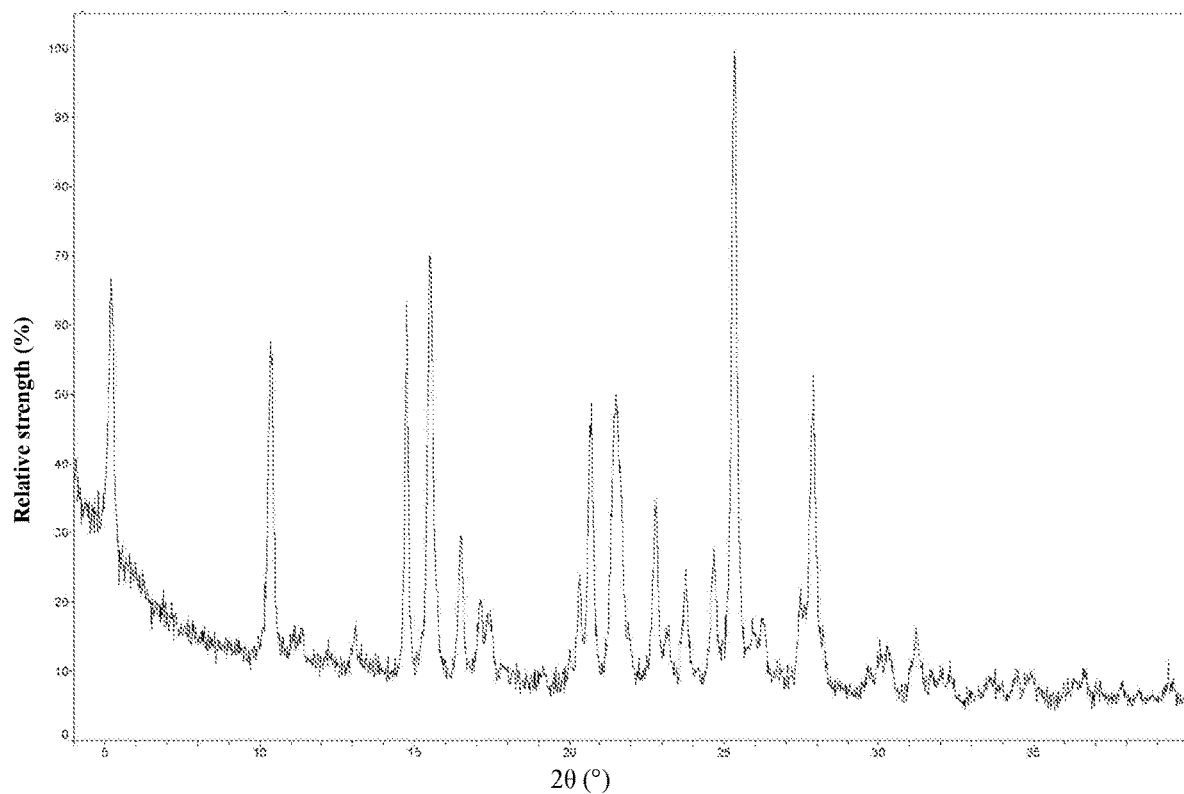
FIG. 4 is an X-ray powder diffraction (XRPD) pattern of the form B crystal of the hydrochloride of formula II in Example 6.

The following specific examples are presented to enable those skilled in the art to more clearly understand and practice the present application. These specific examples should not be considered as limiting the scope of the present application, but merely as being exemplary description and representative of the present application.

All operations involving easily oxidizable or hydrolyzable materials were performed under nitrogen atmosphere. Unless otherwise stated, all starting materials used in the present application were commercially available and used without further purification. The solvents used in the present application are all commercially available and used without special treatment. Compounds are named either manually or by ChemDraw® software, and supplier's catalog names are given for commercially available compounds.

The following abbreviations are used in the present application: DMAP represents 4-dimethylaminopyridine; $Pd_2(dba)_3$ represents tris(dibenzylideneacetone)dipalladium; Xantphos represents 4,5-bis(diphenylphosphino)-9,9-dimethylxanthene; $Pd(dppf)Cl_2$ represents [1,1'-bis(diphenylphosphino)ferrocene]palladium dichloride.

Example 1: Preparation of Compound of Formula I

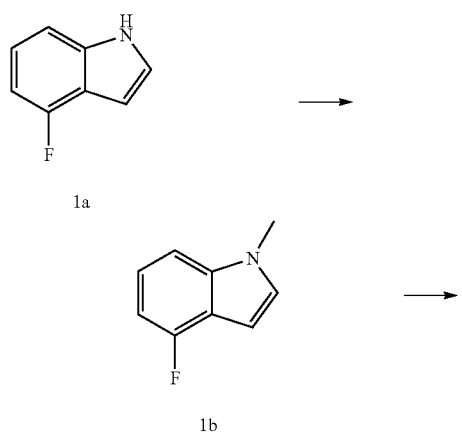

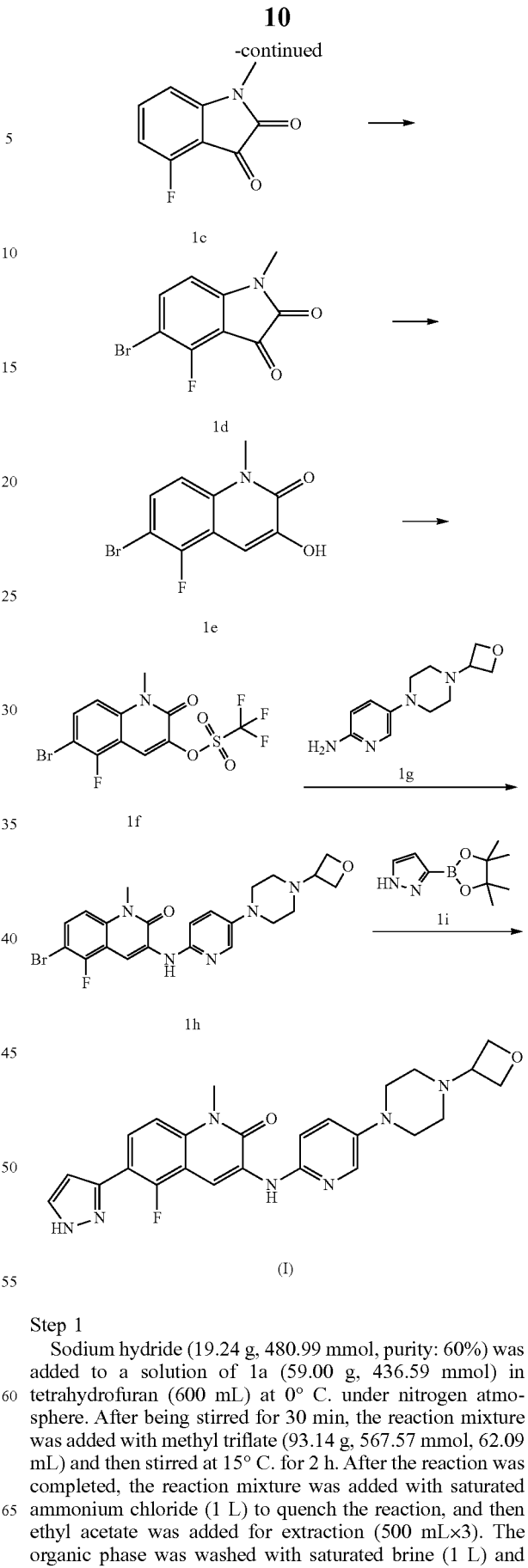

Step 1

Sodium hydride (19.24 g, 480.99 mmol, purity: 60%) was added to a solution of 1a (59.00 g, 436.59 mmol) in tetrahydrofuran (600 mL) at 0° C. under nitrogen atmosphere. After being stirred for 30 min, the reaction mixture was added with methyl triflate (93.14 g, 567.57 mmol, 62.09 mL) and then stirred at 15° C. for 2 h. After the reaction was completed, the reaction mixture was added with saturated ammonium chloride (1 L) to quench the reaction, and then ethyl acetate was added for extraction (500 mL×3). The organic phase was washed with saturated brine (1 L) and dried over anhydrous sodium sulfate. After filtration and concentration, the residue was subjected to column chromatography to give 1b.

$^1$H NMR (400 MHz, CDCl$_3$) δ=7.22-7.08 (m, 2H), 7.03 (br d, J=3.0 Hz, 1H), 6.86-6.73 (m, 1H), 6.58 (d, J=2.5 Hz, 1H), 3.81 (s, 3H).

Step 2

N-bromosuccinimide (65.63 g, 368.72 mmol) was added to a solution of 1b (55.00 g, 368.72 mmol) in dimethyl sulfoxide (400 mL) under nitrogen atmosphere, and the reaction mixture was then stirred at 20° C. for 1 h. After being added with N-bromosuccinimide (65.63 g, 368.72 mmol) again, the reaction mixture was heated to 60° C. and stirred for 10 h. After the reaction was completed, the reaction mixture was poured into water (6 L) and filtered. The filter cake was dissolved in acetone (2 L) and filtered, and the resulting filter cake was washed with acetone (500 mL). After the filtrate was concentrated, the residue was subjected to column chromatography to give 1c.

$^1$H NMR (400 MHz, DMSO-d6) δ=7.72 (dt, J=5.8, 8.2 Hz, 1H), 6.99 (d, J=7.8 Hz, 1H), 6.93 (t, J=8.8 Hz, 1H), 3.15 (s, 3H).

Step 3

N-bromosuccinimide (40.04 g, 224.95 mmol) was added to a solution of 1c (31.0 g, 173.04 mmol) in acetonitrile (300 mL) and water (600 mL) under nitrogen atmosphere, and the reaction mixture was then stirred at 15° C. for 16 h. After the reaction was completed, the reaction mixture was filtered, and the filter cake was washed with water (300 mL) and dried to give 1d.

$^1$H NMR (400 MHz, DMSO-d6) δ=7.99 (dd, J=7.3, 8.3 Hz, 1H), 6.98 (d, J=8.5 Hz, 1H), 3.14 (s, 3H).

Step 4

Trimethylsilyldiazomethane (2 mol/L, 65.11 mL) was added dropwise to a solution of 1d (32.00 g, 124.01 mmol) and triethylamine (25.1 g, 248.02 mmol) in ethanol (300 mL) at 0° C. under nitrogen atmosphere, and the reaction mixture was then stirred at 0-15° C. for 1 h. After the reaction was completed, the reaction mixture was concentrated. The residue was slurried with ethyl acetate (500 mL) and filtered, and the filter cake was dried to give 1e.

$^1$H NMR (400 MHz, DMSO-d6) δ=10.17 (br s, 1H), 7.65 (dd, J=7.5, 9.0 Hz, 1H), 7.30 (d, J=9.0 Hz, 1H), 7.11 (s, 1H), 3.69 (s, 3H).

Step 5

Trifluoromethanesulfonic anhydride (13.48 g, 47.78 mmol) was added dropwise to a solution of 1e (10.0 g, 36.76 mmol), pyridine (8.72 g, 110.27 mmol) and DMAP (449.04 mg, 3.68 mmol) in dichloromethane (200 mL) at 0° C. under nitrogen atmosphere, and the reaction mixture was then stirred at 15° C. for 1 h. After the reaction was completed, the reaction mixture was quenched with water (300 mL), and then adjusted to pH 5 with 1 N hydrochloric acid. The organic phase was washed with saturated sodium chloride (250 mL), dried over anhydrous sodium sulfate, filtered and concentrated to give 1f.

$^1$H NMR (400 MHz, CDCl$_3$) δ=7.93 (s, 1H), 7.82-7.75 (m, 1H), 7.11 (d, J=9.0 Hz, 1H), 3.79 (s, 3H).

Step 6

1f (10.00 g, 24.74 mmol), 1g (6.38 g, 27.21 mmol), Pd$_2$(dba)$_3$ (2.27 g, 2.47 mmol), Xantphos (2.15 g, 3.71 mmol) and cesium carbonate (16.12 g, 49.48 mmol) were added to tetrahydrofuran (200 mL) under nitrogen atmosphere, and the reaction mixture was then stirred at 50° C. for 16 h. After the reaction was completed, the reaction mixture was added to water (200 mL) and filtered, and the filter cake was slurried with ethyl acetate (100 mL). After filtration, the solid was dried to give 1h.

$^1$H NMR (400 MHz, DMSO-d6) δ=9.07-8.76 (m, 2H), 8.00 (br d, J=2.3 Hz, 1H), 7.68-7.40 (m, 2H), 7.32 (br dd, J=9.0, 13.3 Hz, 2H), 4.71-4.39 (m, 4H), 3.75 (s, 3H), 3.52-3.39 (m, 1H), 3.14 (br s, 4H), 2.42 (br s, 4H).

Step 7

1h (9.00 g, 18.43 mmol), potassium carbonate (6.37 g, 46.07 mmol), Pd(dppf)Cl$_2$ (1.08 g, 1.47 mmol) and 1i (5.36 g, 27.64 mmol) were added to 1,4-dioxane (160 mL) and water (40 mL) under nitrogen atmosphere, and the reaction mixture was then stirred at 110° C. for 16 h. After the reaction was completed, the reaction mixture was cooled to precipitate a solid, and then filtered, and the filter cake was washed with water (200 mL) and ethyl acetate (100 mL) and dried to give the compound of formula I.

$^1$H NMR (400 MHz, DMSO-d6) δ=13.08 (br s, 1H), 9.04 (br s, 1H), 8.78 (br s, 1H), 8.16-7.70 (m, 3H), 7.57-7.23 (m, 3H), 6.73 (br s, 1H), 4.74-4.37 (m, 4H), 3.79 (br s, 3H), 3.56 (br s, 2H), 3.14 (br s, 3H), 2.42 (br s, 4H).

Example 2: Preparation of Form A Crystal of Hydrochloride of Formula II

Deionized water (5440 mL) was added into a 50 L reaction kettle and then stirred mechanically at a speed of 200 rpm. After the reaction kettle was heated to an internal temperature of 35-38° C., the compound of formula I (1360 g) was added in batches, and the reaction mixture was stirred for 0.5 h to form yellow suspension. Formic acid (2720 mL) was added dropwise into the reaction kettle over a period of about 1 h until the solution was completely clear, and the resulting reaction mixture was then stirred for 1 h. 1 mol/L prepared aqueous hydrochloric acid solution (4290 mL) was then added dropwise into the reaction kettle over a period of about 2 h, and the reaction mixture, which was still yellow clear liquid, was stirred overnight without changing the conditions. Ethanol (24900 mL) was added dropwise into the reaction kettle over a period of about 5 h, where when about 7000 mL of ethanol was added, a bright yellow solid began to precipitate, and the dropwise addition was continued until the solid was completely precipitated. The reaction mixture was stirred overnight without changing the conditions. The reaction mixture was then filtered, and the filter cake was dried in vacuum to constant weight to give the form A crystal of the hydrochloride of formula II (1220 g, purity: 99.79%).

Example 3: Preparation of Form A Crystal of Hydrochloride of Formula II

Deionized water (2 mL) was added into a 100 mL reaction flask. After the reaction flask was heated to an internal temperature of 35-38° C., the compound of formula I (0.6 g) was added, and the reaction mixture was stirred for 0.5 h to form yellow suspension. Formic acid (1 mL) was added dropwise into the reaction flask over a period of about 5 min until the solution was completely clear, and the resulting reaction mixture was then stirred for 1 h. 1 mol/L prepared aqueous hydrochloric acid solution (1.26 mL) was then added dropwise into the reaction flask over a period of about 5 min, and the reaction mixture, which was still yellow clear liquid, was stirred overnight without changing the conditions. Ethanol (8 mL) was added dropwise into the reaction flask over a period of about 15 min, where when about 5 mL of ethanol was added, a bright yellow solid began to precipitate, and the dropwise addition was continued until the solid was completely precipitated. The reaction mixture was stirred for 4 h without changing the conditions. The reaction mixture was then filtered, and the filter cake was dried in vacuum to constant weight to give the form A crystal of the hydrochloride of formula II (0.55 g).

Example 4: Preparation of Form A Crystal of Hydrochloride of Formula II

Deionized water (2 mL) was added into a 100 mL reaction flask. After the reaction flask was heated to an internal temperature of 35-38° C., the compound of formula I (0.6 g) was added, and the reaction mixture was stirred for 0.5 h to form yellow suspension. Formic acid (1 mL) was added dropwise into the reaction flask over a period of about 5 min until the solution was completely clear, and the resulting reaction mixture was then stirred for 1 h. 1 mol/L prepared aqueous hydrochloric acid solution (2.52 mL) was then added dropwise into the reaction flask over a period of about 5 min, and the reaction mixture, which was still yellow clear liquid, was stirred overnight without changing the conditions. Ethanol (8 mL) was added dropwise into the reaction flask over a period of about 15 min, where when about 5 mL of ethanol was added, a bright yellow solid began to precipitate, and the dropwise addition was continued until the solid was completely precipitated. The reaction mixture was stirred for 4 h without changing the conditions. The reaction mixture was then filtered, and the filter cake was dried in vacuum to constant weight to give the form A crystal of the hydrochloride of formula II (0.55 g).

Example 5: Preparation of Form A Crystal of Hydrochloride of Formula II

Ethyl acetate (2 mL) was added into a 100 mL reaction flask. After the reaction flask was heated to an internal temperature of 35-38° C., the compound of formula I (1.0 g) was added, and the reaction mixture was stirred for 0.5 h to form yellow suspension. Formic acid (3 mL) was added dropwise into the reaction flask over a period of about 15 min until the solution was completely clear, and the resulting reaction mixture was then stirred for 1 h. 35% aqueous hydrochloric acid solution (0.26 mL) and ethyl acetate (2.0 mL) were then added dropwise into the reaction flask over a period of about 5 min, and the reaction mixture, which was still yellow clear liquid, was stirred overnight without changing the conditions. Ethanol (20 mL) was added dropwise into the reaction flask over a period of about 15 min, where when about 15 mL of ethanol was added, a bright yellow solid began to precipitate, and the dropwise addition was continued until the solid was completely precipitated. The reaction mixture was stirred for 4 h without changing the conditions. The reaction mixture was then filtered, and the filter cake was dried in vacuum to constant weight to give the form A crystal of the hydrochloride of formula II (0.95 g).

Example 6: Preparation of Form B Crystal of Hydrochloride of Compound of Formula I The compound of formula I (500 mg) was added into a 40 mL glass vial, and then ethanol (35 mL) was added. After being stirred for 2 h at 40° C. on a magnetic stirrer, the reaction mixture was added with 1.2 mol/L diluted hydrochloric acid (3 mL) 10-fold diluted with water. The resulting reaction mixture was stirred overnight at 40° C. on the magnetic stirrer. The reaction mixture was centrifuged, and the solid was dried in a vacuum drying oven overnight to give the form B crystal of the hydrochloride of formula II.

Example 7: Preparation of Form B Crystal of Hydrochloride of Compound of Formula I The compound of formula I (500 mg) was added into a 40 mL glass vial, and then a mixed solution of ethanol (29.2 mL) and acetic acid (5.8 mL) was added. After being stirred for 2 h at 40° C. on a magnetic stirrer, the reaction mixture was added with 1.2 mol/L diluted hydrochloric acid (3 mL) 10-fold diluted with water. The resulting reaction mixture was stirred overnight at 40° C. on the magnetic stirrer. The reaction mixture was centrifuged, and the solid was dried in a vacuum drying oven overnight to give the form B crystal of the hydrochloride of formula II.

Example 8: Preparation of Form B Crystal of Hydrochloride of Compound of Formula I The compound of formula I (500 mg) was added into a 40 mL glass vial, and then a mixed solution of acetone (29.2 mL) and acetic acid (5.8 mL) was added. After being stirred for 2 h at 40° C. on a magnetic stirrer, the reaction mixture was added with 1.2 mol/L diluted hydrochloric acid (3 mL) 10-fold diluted with water. The resulting reaction mixture was stirred overnight at 40° C. on the magnetic stirrer. The reaction mixture was centrifuged, and the solid was dried in a vacuum drying oven overnight to give the form B crystal of the hydrochloride of formula II.

Experimental Example 1: Study on Stability of Form A Crystal of Hydrochloride of Formula II According to the "Guidelines for the Stability Test of APIs and Preparations" (General Principles 9001 of the Four Parts of the Chinese Pharmacopoeia, 2015 Edition), the stability of the form A crystal of the compound of formula II was investigated at high temperature (60° C., open), high humidity (room temperature/relative humidity 92.5%, open) and illumination (total illuminance of $1.2 \times 10^6$ Lux·hr/near UV energy of 200w·hr/m$^2$, open).

Form A crystal of the hydrochloride of formula II (5 mg) was weighed out, placed at the bottom of a glass sample bottle and spread into a thin layer. The vials in which the samples were placed at high temperature and high humidity were sealed with aluminum foil, and small holes were provided in the aluminum foil to ensure that the samples were sufficiently contacted with atmospheric air. The vial in which the sample was placed under strong light was placed open without sealing with aluminum foil. The samples placed under different conditions were taken and tested for XRPD spectrum on day 5 and day 10. The test results were compared with the initial test results on day 0, and the test results are shown in Table 3 below:

TABLE 3

Experimental results on stability of form A crystal of hydrochloride of formula II

| Experimental condition | Time point | Crystalline form |
| --- | --- | --- |
| High temperature (60° C., open) | Day 0 | Form A crystal |
|  | Day 5 | Form A crystal |
|  | Day 10 | Form A crystal |

TABLE 3-continued

Experimental results on stability of form
A crystal of hydrochloride of formula II

| Experimental condition | Time point | Crystalline form |
|---|---|---|
| High humidity (room temperature/relative humidity 92.5%, open) | Day 5<br>Day 10 | Form A crystal<br>Form A crystal |
| Illumination (total illuminance of $1.2 \times 10^6$ Lux · hr/near UV energy of 200 w · hr/m$^2$, open) | | Form A crystal |

The results show that the form A crystal of hydrochloride of formula II has good stability under the conditions of high temperature, high humidity and illumination.

Figure 5:
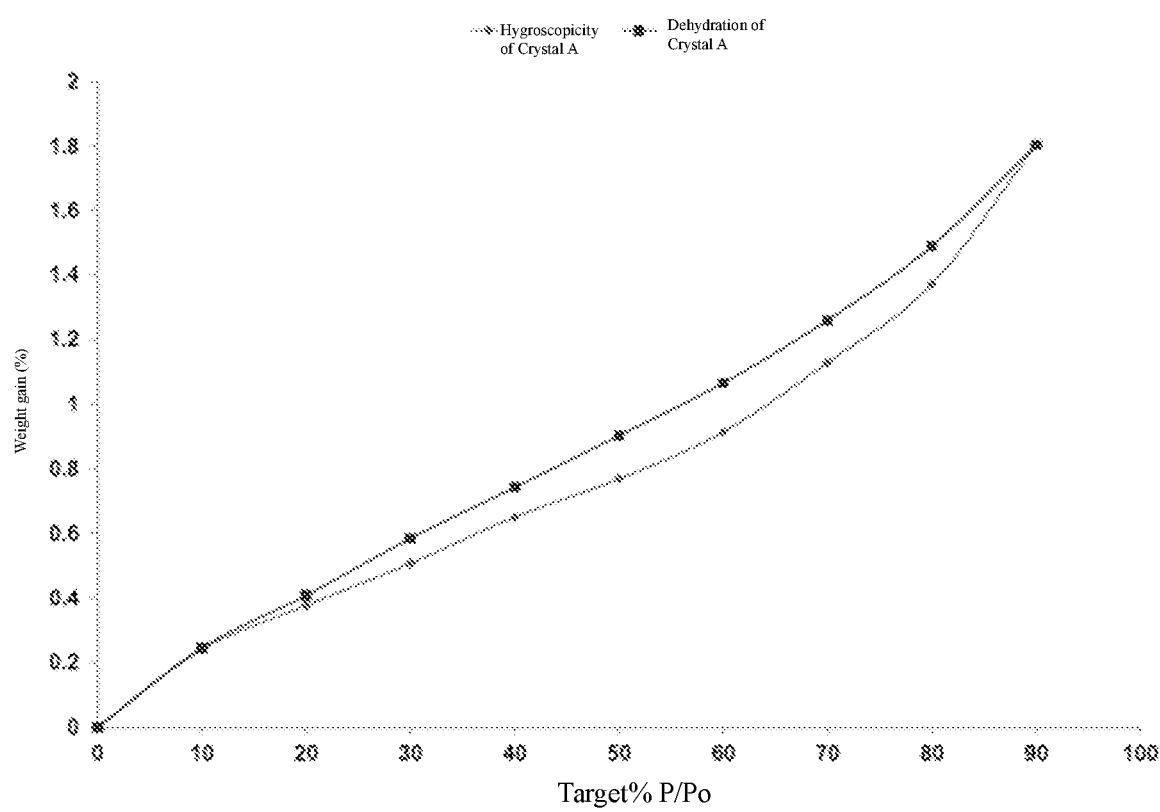
FIG. 5 is a dynamic vapor sorption (DVS) pattern of the form A crystal of the hydrochloride of formula II in Example 2.

Experimental Example 2: Study on Hygroscopicity of Form A Crystal of Hydrochloride of Formula II Instrument: SMS DVS Advantage;
Method: placing 10-15 mg of the form A crystal of hydrochloride of formula II in a DVS sample tray for testing;
The DVS parameters are as follows:
Temperature: 25° C.
Balancing: dm/dt=0.01%/min (shortest: 10 min, longest: 180 min)
drying: drying at 0% RH for 120 min
RH (%) test gradient: 10%
Range of RH (%) test gradient: 0%-90%-0%
Results: a DVS pattern of the form A crystal of hydrochloride of formula II is shown in FIG. 5, where ΔW=1.371%;
Conclusion: the form A crystal of hydrochloride of formula II is less hygroscopic at 25±1° C. and 80±2% RH.

Experimental Example 3: Study on Stability of Form A Crystal of Hydrochloride of Formula II in Organic Solvent Form A crystal of hydrochloride of formula II (60 mg) was weighed out and placed into an 8 mL glass vial. After being added with methanol (4 mL), the glass vial was placed on a magnetic stirrer, and the mixture was stirred at 20° C. and 50° C., each for 24 h. The suspension was centrifuged to remove the organic solvent, and the resulting solid was dried in vacuum and then tested for XRPD spectrum, which was compared with the XRPD spectrum of the form A crystal of hydrochloride of formula II.

According to the above method, ethanol, ethyl acetate, acetone, acetonitrile, tetrahydrofuran, 1,4-dioxane and n-hexane were used as solvents to conduct parallel tests.

The results show that the XRPD spectrum of the form A crystal of hydrochloride of formula II doesn't change after it is suspended in the above solvent for 24 h, suggesting that no transformation of crystalline form occurs for the form A crystal of hydrochloride of formula II in the investigated solvent system and its crystalline form is relatively stable.

Experimental Example 4: In Vitro Test of Syk Kinase Inhibition by Compound of Formula I 4.1 Purpose of experiment: to detect the interaction between the substrate and the enzyme by homogeneous time-resolved fluorescence (HTRF) technology, and evaluate the inhibition of the compound on tyrosine kinase (Syk) by taking the half-inhibitory concentration ($IC_{50}$) value of the compound as an index.

4.2 Experimental Materials:
Tyrosine kinase (Invitrogen, PV3857)
Dithiothreitol (DTT) (Sigma #43815)
Adenosine Triphosphate (ATP) (Sigma #A7699)
Magnesium chloride ($MgCl_2$) (Sigma #63020)
Manganese chloride ($MnCl_2$) (Sigma #M1787)
Ethylenediaminetetraacetic acid (EDTA) (Invitrogen #15575-020)
4-hydroxyethylpiperazine ethanesulfonic acid buffer (HEPES buffer) (Invitrogen #15630-080)
HTRF@ KinEASE™ tyrosine kinase kit (Cisbio #62TK0PEC, 20000 tests)
Low volume, 384-well, white polystyrene plate (Greiner #784075)
384 microplate (Greiner #781946)
Centrifuge (Eppendorf #5810R)
Pipettor (Eppendorf)
Pipette (Greiner)
Pipetting gun (Eppendorf)
Multidrop automatic dispenser
POD 810 Plate Assembler, a fully automated microplate pretreatment system
Envision Reader, a multifunctional microplate reader 4.3 Experimental Procedures and Method:
a) Dilution and Application of Compound
 1) The powder of the compound of formula I was weighed out and dissolved in a certain amount of dimethyl sulfoxide, and the initial concentration was 10 mM;
 2) The compound concentration was diluted to 0.74 mM, and sample addition was performed using a fully automated microplate pretreatment system at 135 nL per well. The initial concentration of the compound was 10 μM, and 11 concentration points were obtained after a 3-fold decreasing gradient dilution.
b) Reaction of Enzyme with Substrate
 1) Prepared to dilute the experiment buffer. The 5×HTRF buffer in the kit was diluted to 1×, and a specified amount of DTT and $MgCl_2$ solution was added according to the kit manual for later use;
 2) A tyrosinase reaction solution was prepared with 1×HTRF buffer, and the final reaction concentration of the tyrosine kinase was 0.0156 ng/μL;
 3) A mixed solution of tyrosine kinase-substrate-biotin/ATP was prepared, and the final substrate concentration was 0.2 μM and the ATP concentration was 2 μM;
 4) The tyrosinase solution and the mixed solution of tyrosine kinase-substrate-biotin/ATP were added into a microplate with the compound of formula I at 5 μL per well by using a Multidrop automatic dispenser, and the mixture was incubated at 23° C. for 1 h.
c) Detection
 1) An EDTA solution (13.33 mL) was added into a detection buffer in a kit, and then a specified amount of uranium (Eu) labeled antibody and streptavidin XL-665 were added according to kit manual to prepare a detection solution;
 2) The detection solution (10 μL) was added to each well of the above microplate by using a Multidrop automatic dispenser, and the resulting mixture was incubated at 23° C. for 1 h to stop the reaction of the enzyme with the mixed solution of substrate;
 3) After centrifugation, the resulting supernatant was read on a multifunctional microplate reader.
d) Data Analysis
 The data were analyzed using XL-Fit to calculate the $IC_{50}$ value for the compound of formula I.

Experimental Example 5: In Vitro Test of Inhibition on AKT Phosphorylation by Compound of Formula I 5.1 Purpose of experiment: to detect the protein kinase AKT phosphorylation in cells by enzyme-linked immunosorbent assay (ELISA), and evaluate the inhibition of the compound on the AKT phosphorylation by taking the half-inhibitory concentration ($IC_{50}$) value of the compound as an index.

5.2 Experimental Materials

Cell line: Ramoscell line
Cell culture medium (RPMI1640, Invitrogen #22400-105; 10% fetal bovine serum, Gibco #10099-141; L-glutamine 1×, Gibco #25030-081)
Medium for experiment (serum-free, RPMI 1640, Invitrogen #22400-105; L-glutamine 1×, Gibco #25030)
Lysis buffer (Tris-HCl, Invitrogen 15567-1000 mL; NaCl, domestic; sodium deoxycholate, Sigma 30970-25G; polyethylene glycol octylphenyl ether, Sigma T9284-100 mL; sodium dodecyl sulfonate, Sigma L3771; EDTA, Invitrogen 15575-038-100 mL; ultrapure water, MilliQ)
Protease inhibitor (Roche, 4693159001-30/BOX)
Phosphatase inhibitor mixture 2 (Sigma, P5726-5 ML)
Phosphatase inhibitor mixture 3 (Sigma, P0044-5 ML)
Goat anti-human immunoglobulin M (F(ab')2 Goat Anti-Human IgM) (JacksonImmuno Research-109-006-129)
Phosphorylation AKT detection kit (Phospho-AKT 1/2/3 (ser473)) (TGR Bioscience, EKT002)
10× Hank's balanced salt solution (Gibco #14065-056)
96-well cell plate (Greiner #655090)
Compound V-well dilution plate (Axygen #WITP02280)
$CO_2$ incubator (Thermo #371)
Centrifuge (Eppendorf #5810R)
Vi-cell cell counter (Beckman Coulter)
Pipettor (Eppendorf)
Pipette (Greiner)
Pipetting gun (Eppendorf)
Multifunctional microplate reader (Envision Reader)

5.3 Experimental Procedures and Method a) Cell Seeding (Ramos Cells)
  1) A cell culture medium was preheated in a water bath at 37° C., and Ramos suspended cell culture was pipetted and centrifuged for 5 min at 1000 rpm;
  2) After the supernatant was pipetted away after centrifugation, the preheated cell culture medium (10 mL) was added into the centrifuge tube. The cells were resuspended by pipetting, and then Ramos cell resuspension (1 mL) was pipetted and subjected to cell counting with Vi-cell cell counter;
  3) The Ramos cell resuspension was diluted with cell culture medium to a cell density of $5\times10^6$ cells/mL, and the diluted cells were added to a 96-well cell culture plate (100 µL/well) with a pipetting gun; the cell culture plate was incubated overnight in an incubator at 37° C., 5% CO2.

b) Cell Starvation
  After being cultured overnight, the seeded cells were centrifuged at 1000 rpm for 5 min the next day. The original cell culture medium was pipetted away, and then a serum-free medium for experiment was added. The cell culture plate was placed in an incubator at 37° C., 5% CO2, and cells were starved overnight.

c) Preparation and Application of Test Sample
  1) The compound of formula I, as a test sample, was dissolved in dimethyl sulfoxide to obtain a solution of the compound of formula I with an initial concentration of 5 mM; three-fold gradient dilution of the solution was performed using a compound V-well dilution plate to obtain 10 concentration points;
  2) Another new compound V-well dilution plate was added with serum-free medium for experiment at 198 µL per well, and then the solution with the initial concentration (2 µL) and each compound solution after three-fold gradient dilution (2 µL) were added into wells respectively, and the mixtures were mixed well by a pipetting gun; at this time, the compound was 100-fold diluted, wherein the maximum concentration of the diluted compound of formula I in the well was 50 µM;
  3) Each diluted compound solution obtained in step 2) was added to the cell culture plate starved overnight in b) at 25 µL per well, wherein the cell culture medium in each well was 100 µL, and each compound solution was 5-fold diluted; at this time, the maximum concentration of the diluted compound of formula I in the well was 10 M, and in other wells were the diluted solutions of the compound of the formula I in 10 concentration points obtained by 3-fold gradient dilution;
  4) The cell culture plate of step 3) was centrifuged at 1000 rpm for 1 min, and then placed in an incubator at 37° C., 5% CO2 to allow the compound to react for 1 h.

d) Stimulation with Stimulating Factor
  1) Two tubes of 1× balanced salt solution were prepared by diluting 10× balanced salt solution to 1× balanced salt solution with double distilled water, and respectively placed in a 37° C. thermostat and a 4° C. refrigerator for later use;
  2) A tube of mixed solution for lysis was prepared and placed in a 4° C. refrigerator for later use. The formula was as follows: 1 protease inhibitor tablet+100 µL of phosphatase inhibitor mixture 2+100 µL of phosphatase inhibitor mixture 3+10 mL of lysis buffer;
  3) Goat anti-human immunoglobulin M (F(ab')2 Goat Anti-Human IgM) (1.2 mg/mL) was diluted to 60 µg/mL with 1× balanced salt solution preheated at 37° C.;
  4) After one hour of treatment of Ramos cells with compound, diluted goat anti-human immunoglobulin M (F(ab')2 Goat Anti-Human IgM) (25 µL) was added per well, wherein the action concentration of the IgM at this time was 10 µg/mL;
  5) The cells were stimulated by the IgM for 10 min, and then centrifuged at 4000 rpm for 5 min to deposit suspended cells at the bottom of the 96-well plate. The liquid in the 96-well plate was slightly poured away without pouring away the suspended cells, and the residual liquid was absorbed away using a paper towel;
  6) The stimulation of the cells by IgM was terminated by adding pre-cooled (4° C.) 1× balanced salt solution (250 µL) to each well and centrifuging the mixture at 4000 rpm for 5 min.

e) Preparation of Cell Lysate
  1) The liquid in the 96-well plate was gently poured away and the residual liquid was absorbed away using a paper towel; the mixed solution for lysis (100 µL) was added into each well and the mixture was shaken on a shaker at 4° C. for 1 h to lyse cells;
  2) After cell lysis for 1 h, the cells were centrifuged at 4000 rpm for 5 min at 4° C., and the supernatant was gently pipetted away, thus obtaining the cell lysate.

f) Enzyme-Linked Immunosorbent Assay (ELISA)
  1) A 96-well Elisa plate in the phosphorylated AKT detection kit was balanced to room temperature and added with cell lysate at 50 µL per well;

2) The capture antibody reagent and detection antibody reagent in the kit were mixed in a ratio of 1:1, and then the mixture was added into the 96-well Elisa plate at 50 µL per well; the resulting mixed solution of the cell lysate and the antibody reagent mixture was shaken on a shaker at room temperature for 1 h;
3) The washing solution (10×) in the kit was diluted to 1× by double distilled water; the liquid in the Elisa plate was poured away and the plate was patted dry on absorbent paper; the 1× washing solution (200 µL) was added into each well for washing and then the plate was patted dry, and the process was repeated for 4 times;
4) Substrate 10-acetyl-3,7-dihydroxyphenazine (ADHP) (100×) was diluted to 1× with ADHP diluent and then added to the 96-well Elisa plate at 100 µL per well, and the mixture was shaken on a shaker at room temperature for 10 min;
5) Stop solution (10 µL) was added into each well, and the mixture was centrifuged instantaneously, shaken for 5 min at room temperature, and read on an Envision Reader multifunctional microplate reader.

g) Data Analysis

The data were analyzed using XL-Fit to calculate the $IC_{50}$ value for the compound.

The results of Experimental Example 4 and Experimental Example 5 are shown in Table 4.

TABLE 4

| Sample | Syk | |
|---|---|---|
| | $IC_{50}$ on inhibition of Syk kinase (nM) | $IC_{50}$ on inhibition of AKT phosphorylation (nM) |
| Compound of formula I | 12 | 170 |

What is claimed is:

1. A hydrochloride of a compound of formula I,

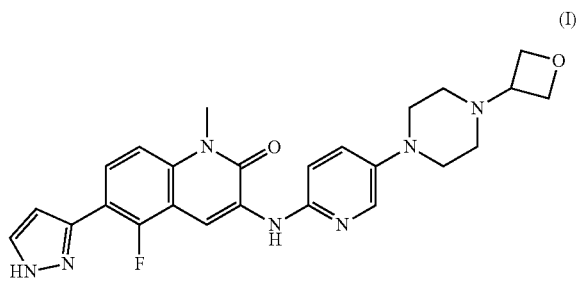 [SMILES: Cn1c(=O)c(Nc2ccc(N3CCN(C4COC4)CC3)cn2)cc2c(F)c(-c3cc[nH]n3)ccc21]

(I)

wherein the hydrochloride is in a crystalline form selected from the group consisting of a form A crystal and a form B crystal,
the form A crystal is characterized by having diffraction peaks represented by 2θ values at about 4.9°, 10.1°, 12.2°, 15.5°, 19.6° and 23.8° in an X-ray powder diffraction spectrum,
the form B crystal is characterized by having diffraction peaks represented by 2θ values at about 5.2°, 10.4°, 14.7°, 15.5° and 25.3° in an X-ray powder diffraction spectrum.

2. The hydrochloride of the compound of formula I according to claim 1, wherein the hydrochloride is a 1:1 hydrochloride of the compound of formula I.

3. The hydrochloride of the compound of formula I according to claim 1, wherein the hydrochloride is the form A crystal characterized by having diffraction peaks represented by 2θ values at about 4.9°, 10.1°, 12.2°, 15.5°, 17.8°, 19.2°, 19.6°, 22.9°, 23.8° and 25.6° in an X-ray powder diffraction spectrum.

4. The hydrochloride of the compound of formula I according to claim 3, wherein the hydrochloride is the form A crystal characterized by having diffraction peaks represented by 2θ values at about 4.9°, 9.6°, 10.1°, 12.2°, 15.5°, 16.3°, 17.8°, 19.2°, 19.6°, 20.4°, 22.9°, 23.3°, 23.8°, 25.6°, 26.8°, 27.4°, 29.0° and 36.8° in an X-ray powder diffraction spectrum.

5. The hydrochloride of the compound of formula I according to claim 4, wherein the hydrochloride is the form A crystal characterized by having diffraction peaks represented by 2θ values at about 4.9°, 9.6°, 10.1°, 12.2°, 14.4°, 15.5°, 16.3°, 17.3°, 17.8°, 19.2°, 19.6°, 20.4°, 22.9°, 23.3°, 23.8°, 25.6°, 26.8°, 27.4°, 28.3°, 29.0°, 31.2°, 31.6°, 31.9°, 32.3°, 33.0°, 34.3° and 36.8° in an X-ray powder diffraction spectrum.

6. The hydrochloride of the compound of formula I according to claim 1, wherein the hydrochloride is the form A crystal characterized by having an absorption peak at about 272° C. in a differential scanning calorimetry (DSC) pattern.

7. The hydrochloride of the compound of formula I according to claim 1, wherein the hydrochloride is the form B crystal characterized by having diffraction peaks represented by 2θ values at about 5.2°, 10.4°, 14.7°, 15.5°, 16.5°, 20.7°, 21.5°, 22.8°, 25.3° and 27.9° in an X-ray powder diffraction spectrum.

8. The hydrochloride of the compound of formula I according to claim 7, wherein the hydrochloride is the form B crystal characterized by having diffraction peaks represented by 2θ values at about 5.2°, 10.4°, 14.7°, 15.5°, 16.5°, 17.1°, 17.5°, 20.3°, 20.7°, 21.5°, 22.8°, 23.8°, 24.7°, 25.3°, 27.5°, 27.9° and 31.2° in an X-ray powder diffraction spectrum.

9. The hydrochloride of the compound of formula I according to claim 8, wherein the hydrochloride is the form B crystal characterized by having diffraction peaks represented by 2θ values at about 5.2°, 10.4°, 13.1°, 14.7°, 15.5°, 16.5°, 17.1°, 17.5°, 20.0°, 20.3°, 20.7°, 21.5°, 22.8°, 23.2°, 23.8°, 24.7°, 25.3°, 25.9°, 26.2°, 27.5°, 27.9°, 28.2°, 29.7°, 30.0°, 30.3°, 31.2°, 31.7°, 32.3°, 34.5°, 34.9° and 36.6° in an X-ray powder diffraction spectrum.

10. The hydrochloride of the compound of formula I according to claim 1, wherein the form A crystal of the hydrochloride of the compound of formula I accounts for 50% or more of the weight of the hydrochloride of the compound of formula I.

11. The hydrochloride of the compound of formula I according to claim 1, wherein the form B crystal of the hydrochloride of the compound of formula I accounts for 50% or more of the weight of the hydrochloride of the compound of formula I.

12. A pharmaceutical composition comprising the hydrochloride of the compound of formula I according to claim 1.

13. A method for preparing the hydrochloride of the compound of formula I according to claim 1, comprising: (1) adding the compound of formula I into a preheated solvent, then adding another solvent dropwise until the solution is clear, and stirring while maintaining the temperature; (2) adding diluted hydrochloric acid dropwise into the solution of step (1), and stirring overnight while maintaining the temperature; and (3) slowly adding a solvent dropwise into the solution of step (2), stirring to precipitate a solid, filtering, and drying to give the form A crystal of the hydrochloride of the compound of formula I.

14. A method for preparing the hydrochloride of the compound of formula I according to claim 1, comprising: (1) adding the compound of formula I into a solvent and stirring for dissolving; (2) adding diluted hydrochloric acid into the solution of step (1) and stirring overnight; and (3) centrifuging the solution of step (2), and drying the solid to give the form B crystal of the hydrochloride of the compound of formula I.

15. A method for treating a disease related to Syk receptor, comprising administering to a mammal in need thereof the hydrochloride of the compound of formula I according to claim 1.

16. The method according to claim 15, wherein the disease related to Syk receptor is selected from cancer and inflammatory diseases.

17. The method according to claim 15, wherein the disease related to Syk receptor is selected from B-cell lymphoma, Hodgkin's lymphoma, non-Hodgkin's lymphoma, hairy cell leukemia, multiple myeloma, chronic granulocytic leukemia, acute granulocytic leukemia, chronic lymphocytic leukemia, acute lymphocytic leukemia, rheumatoid arthritis, allergic rhinitis, chronic obstructive pulmonary disease (COPD), adult respiratory distress syndrome (ARDs), allergy-induced inflammatory diseases, multiple sclerosis, autoimmune diseases, acute inflammatory reactions, allergic disorders and polycystic kidney disease.

* * * * *